United States Patent [19]
Müller et al.

[11] Patent Number: 5,359,417
[45] Date of Patent: Oct. 25, 1994

[54] SURGICAL MICROSCOPE FOR CONDUCTING COMPUTER-SUPPORTED STEREOTACTIC MICROSURGERY AND A METHOD FOR OPERATING THE SAME

[75] Inventors: Werner Müller, Essingen; Joachim Luber, Essingen/Forst, both of Fed. Rep. of Germany

[73] Assignee: Carl-Zeiss-Stiftung, Heidenheim

[21] Appl. No.: 961,339

[22] Filed: Oct. 15, 1992

[30] Foreign Application Priority Data

Oct. 18, 1991 [DE] Fed. Rep. of Germany ....... 4134481

[51] Int. Cl.$^5$ ..................... G02B 21/22; G02B 11/14; G01B 11/14
[52] U.S. Cl. ................. 356/375; 250/201.3; 359/389
[58] Field of Search .............. 356/328, 375; 250/201.3, 201.6; 364/413.01; 359/376, 377, 389

[56] References Cited

U.S. PATENT DOCUMENTS 4,722,056  1/1988  Roberts et al.
5,273,039  12/1993  Fujiwara et al. ................ 128/653.1

FOREIGN PATENT DOCUMENTS 4032207  4/1991  Fed. Rep. of Germany .

*Primary Examiner*—F. L. Evans
*Assistant Examiner*—Peter J. Rashid
*Attorney, Agent, or Firm*—Walter Ottesen

[57] ABSTRACT

A defined determination of the field of view observed through a surgical microscope is made. To achieve this determination, the relative current position of the plane of the field of view to the position of an object detail of interest is detected in a sighting method with the aid of a position detection system operating according to the laser triangulation principle. As soon as the plane of the field of view and the object detail are coincident, then with the aid of detected optical system data, the position of the object detail with reference to the surgical microscope is determined and, with the detected coordinates of the surgical microscope, the position of the field of view is determined in space. The position detecting system required for this purpose operates on an optical basis and can be integrated into the optics of the surgical microscope.

14 Claims, 4 Drawing Sheets

SURGICAL MICROSCOPE FOR CONDUCTING COMPUTER-SUPPORTED STEREOTACTIC MICROSURGERY AND A METHOD FOR OPERATING THE SAME

BACKGROUND OF THE INVENTION

In conventional microsurgery conducted with the aid of a surgical microscope, problems often occur with respect of the interpretation of the field of view observed through the surgical microscope. The field of view is the instantaneously viewed anatomic situation. The task is then often presented to correlate diagnostic data obtained via various image-producing investigative methods (computer-tomography CT, nuclear magnetic resonance NMR and the like) to the instantaneous observed field of view in order to undertake a specific surgical step. The interpretation and analysis of the field of view provided by the microscope is therefore difficult and time consuming for the surgeon.

An effort to solve this difficulty is based on the use of stereotactic methods in order to make possible a rapid use of the diagnostic data during surgery. Thus, U.S. Pat. No. 4,722,056 discloses a surgical microscope and a method of operating the same wherein images from a preoperative diagnostic method can be superposed on the observed field of view with the aid of an in-reflecting device. The correlation between the surgical microscope and the patient, that is, the determination of the coordinates of the observed field of view is provided here by the determination of the surgical microscope spatial coordinates with the aid of an ultrasonic scanning system. From the spatial coordinates of the surgical microscope, a conclusion is drawn as to the position of the field of view in space from the particular actual optical system data. Here, it can be assumed that the optic detail of interest lies in the plane of the field of view.

This method of localizing the field of view and correlating the same to the corresponding diagnostic data does however have significant disadvantages. Thus, imaging through the optical system of the surgical microscope is always burdened with a certain depth of field which, for magnifications which are customary in neurosurgery, can be in the range of less than tenths of millimeter up to several centimeters. If an anatomic detail becomes of interest to the surgeon during the course of surgery, then the surgeon focuses the microscope on the corresponding location but must take into consideration a certain imprecision between the object detail of interest and the focus plane because of the above-mentioned depth of field, the surgeon's own possible accommodation as well as optical tolerances in the system. Such an arrangement permits no highly precise direct measurement of detail of the object of interest. A reliable target location with the aid of the surgical microscope is likewise not guaranteed. A further disadvantage of this arrangement is the complex configuration of the ultrasonic scanning system at the surgical microscope which hinders the surgeon during surgery.

A similar solution to this problem is disclosed in published German patent application 4,032,207. Here, the exact spatial position of the surgical microscope, which is supported by an articulated linkage mechanism, is determined via the detectors in this mechanism. These detectors detect movement directions and distances of the movable elements. The precise position of the observed field of view in space is computed by determining the coordinates of the surgical microscope from the detector signals as well as from the detected data of the optical system such as the instantaneous focusing state. The determination of the position of the field of view solely from the data of the optical system after successful focusing on the object detail of interest is here associated with the same inaccuracies which were described above. The depth of field problematic, physiological realization characteristics as well as optical tolerances in the system here too prevent a precise determination of position of the observed field of view and especially a direct measurement thereof.

SUMMARY OF THE INVENTION

It is an object of the invention to provide a surgical microscope as well as a method for operating the same which permit the observed field of view to be precisely detected with respect to its coordinates and therefore make possible the correlation with the corresponding diagnostic data from image-yielding diagnostic methods. The precision of the coordinate detection is intended to be dependent upon the resolution limit of the particular image-yielding diagnostic method. Furthermore, the essential components are integrated into the optics of the surgical microscope.

The method of the invention is for operating a surgical microscope arrangement for computer-supported stereotactic microsurgery. The arrangement includes a surgical stereomicroscope having an optical system with two viewing beam paths for viewing a detail of an object defining an object detail plane passing through the object detail. The method includes the steps of: continuously determining the spatial coordinates and the orientation of the surgical stereomicroscope and supply a first signal indicative thereof to a process control unit; continuously detecting the current position of the object plane via an optical position detection system and supplying a second signal indicative thereof to the process control unit; applying the output of the process control unit to an image-processing unit for converting the output into display signals graphically displaying the current position of the object detail plane on a TV-display as a first display; graphically displaying the current position of the plane of the field of view observed through the surgical stereomicroscope on the TV-display as a second display via the process-control unit and the image-processing unit; focusing or defocusing the optical system of the surgical stereomicroscope to bring the first and second displays into overlapping alignment with each other; determining the optical system data of the optical system utilizing detectors monitoring the optical system and supplying a third signal indicative thereof to the process control unit; determining the position of the object detail plane relative to the surgical stereomicroscope with the aid of the optical system data; and, determining the spatial coordinates of the object detail plane from the following: the coordinates of the object detail plane relative to the surgical stereomicroscope, the spatial coordinates of the surgical stereomicroscope and the orientation of the surgical stereomicroscope after a coordinate transformation.

An essential characteristic of the invention is that a selected and marked object detail is brought into superposition with the particular plane of the field of view via a sighting method. If this is ensured, then the relative position of the object detail forward of the surgical microscope is determined from the optical system data of the surgical microscope. In this connection, the knowledge of the precise spatial coordinates and the orientation of the surgical microscope is necessary. The arrangement of the surgical microscope of the invention on a multi-link stand is advantageous for this purpose. Suitable displacement and angle detectors in this multi-link stand enable the position and orientation of the surgical microscope to be precisely detected. When the precise spatial position of the surgical microscope is known, then a conclusion can be drawn as to the position of the observed object detail or of the observed field of view in the patient coordinate system from this precise spatial position together with the result of a previous calibration method. In such a calibration measurement, known points in the patient coordinate system can be measured via the described sighting method. These points in the patient coordinate system are likewise detected via the image-yielding diagnostic method. A diagnostic image corresponding to the position and magnitude of the detected field of view can be provided from the diagnostic data assembled prior to surgery. This diagnostic image can then be reflected into the viewing beam path via a corresponding in-reflecting device. In this way, a superposition of the diagnostic image and the observed field of view is possible. Alternatively, such a display can also take place on a separate diagnostic monitor. In this way, the computer-supported stereotactic use of the surgical microscope is ensured.

Such a sighting method is made possible in that markings are reflected into the viewing beam path which make clear the relative position of the plane of the field of view as well as the position of a laser beam projected onto an object detail. For this purpose, the precise position of the plane of the field of view of the surgical microscope is determined with the aid of a position-detecting system having an optics basis, for example according to the laser-triangulation principle. The position of a laser beam scattered from the surface of the object is evaluated for this purpose on a position-resolving detector. Each change in the spacing between object and microscope or in the focusing of the microscope leads to a lateral displacement of the imaged laser beam on the position-resolving detector. The actual position of the laser beam detected with the aid of a special process control as well as the desired position is displayed via an image-processing arrangement on a TV-display when there is coincidence of the plane of the field of view and the object detail and is reflected into the viewing beam path of the surgical microscope.

By focusing or defocusing the surgical microscope, an effort is made to bring these two marks so that they precisely overlap each other whereby a defined field of view marking (that is, the definite position of the object detail) is ensured. The focusing can take place via an intercept distance variation of the objective system used. However, it is also possible to displace the complete surgical microscope along the optical axis. Only after this sighting method, the precise position of the object detail marked in this manner is determined from the optical-system data. The optical-system data and especially the actual magnification of the magnification system and the adjusted focal length of the primary objective can be detected with suitable distance and/or angle detectors on the drive units for the particular setting. In this way, the relative position of the observed object detail to the surgical microscope is precisely defined. The precise position of the object detail in the patient coordinate system can then be determined together with the spatial coordinates of the surgical microscope and a necessary previous calibration on the patient.

An advantageous processing of the information determined in this manner is in the correlation of the detected field of view defined now with respect to position and orientation together with corresponding diagnostic images (CT, NMR, and the like). These diagnostic images can be superposed on the image section viewed while considering the actual surgical microscope-system data in that the diagnostic images are reflected into the viewing-beam path.

Furthermore, it has been shown to be advantageous to include in a reference measurement the mechanical tolerances of the magnification system and the mechanical tolerances of the focusing as well as adjusting errors of the optical system (such as those occurring during assembly of a surgical microscope of this kind) and to consider the same in the process control. During focusing of the optical system, the errors detected in the reference measurement are continuously considered when determining the coordinates of both the actual plane of the field of view and of marked object detail and are correspondingly corrected for graphical display.

It has likewise been shown advantageous to reflect-in the graphic marks between the binocular tube and the magnification changer.

The position-detecting system according to the laser-triangulation principle operates most advantageously in the non-visible spectral range such as in the near infrared. In this way, a laser with high capacity need not be used which would have been necessary in view of the high illumination intensity in the field of view of the surgical microscope in order to clearly localize the projected laser beam on the object. Furthermore, with an appropriately sensitive position detector, it is ensured that this detector only processes the information of the laser beam of interest and not false information caused by scattered light.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
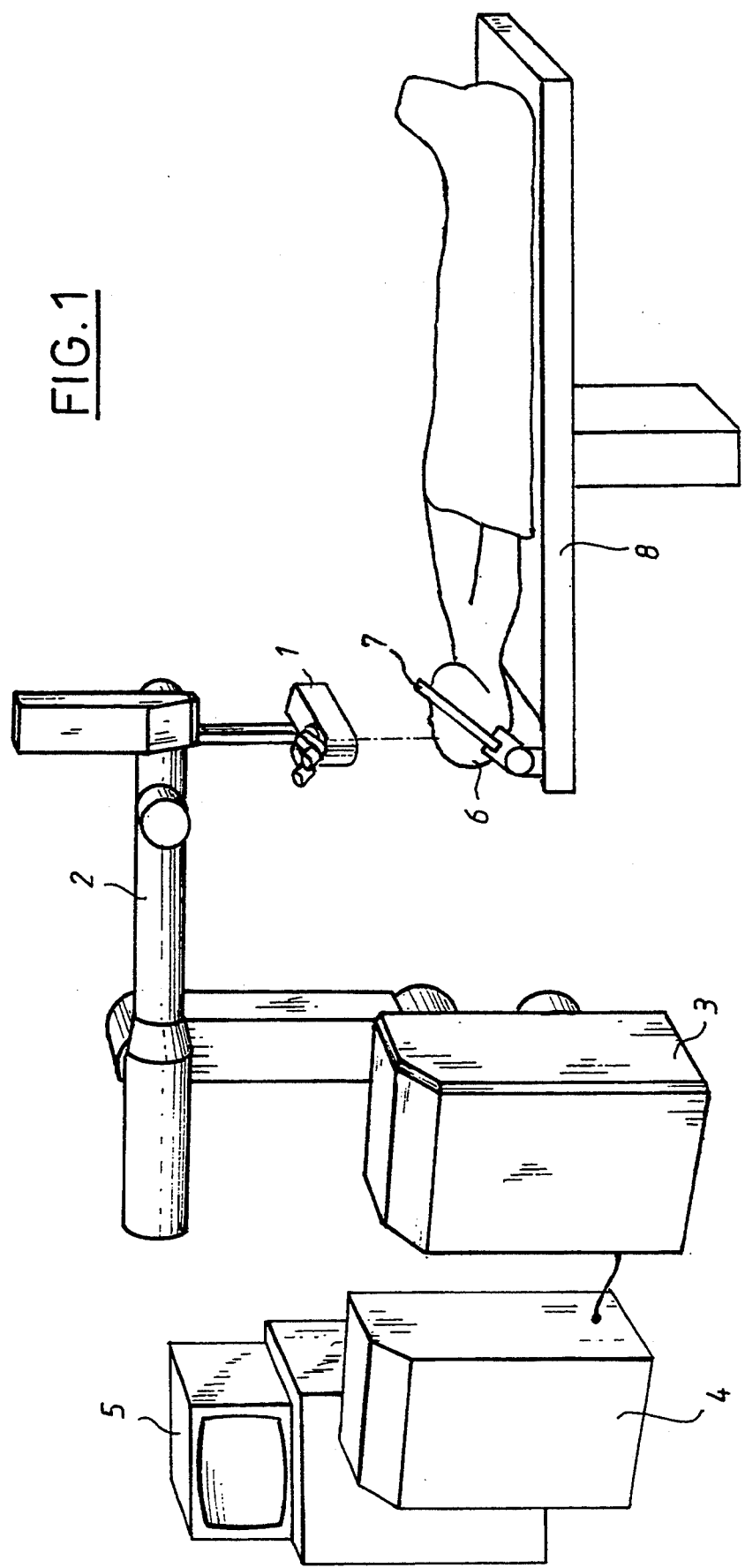
FIG. 1 shows an arrangement of the surgical microscope according to the invention mounted on a suitable multi-link supporting stand.

FIG. 1 shows an arrangement for the use of the surgical microscope 1 according to the invention for computer-supported stereotactic microsurgery. The surgical microscope 1 is securely mounted on a special multi-link supporting stand 2 which enables the surgical microscope 1 to be manipulated in all six degrees of freedom. Most significant for the multi-link supporting stand 2 used here is that the actual spatial coordinates as well as the orientation of the microscope 1 mounted thereon can always be detected by the built-in displacement and angle detectors. A computer operates as a process-control unit 3 and determines the spatial coordinates and orientation of the surgical microscope from the supplied detector signals. The built-in displacement and angle detectors are represented schematically by block 42 in FIG. 2. The process-control unit 3 is mounted in the base part of the multi-link supporting stand 2. An image-processing unit 4 is connected to the process-control unit 3 and graphically converts the signals of the position-detecting system to a TV-display 31 shown in FIG. 2. This TV-display can be integrated into the viewing beam path of the surgical microscope.

The observed field of view can be displayed on a diagnostic monitor 5 via a corresponding camera output of the surgical microscope 1 and can, for example, be superposed with a diagnostic image reconstructed during the surgery after the coordinates and the position of the field of view are determined. This reconstructed diagnostic image can, alternatively, and as already mentioned, be displayed via the TV-display in the viewing beam path of the surgical microscope 1. The image-processing unit 4 takes over the reconstruction of the diagnostic image to be displayed from the diagnostic data record prepared preoperatively. In this way, an on-line use of diagnostic data is possible as the surgeon performs the surgery.

To ensure a reproducible position of the head of the patient during surgery, for example, during brain surgery, the head 6 of the patient lying on the operating table 8 is fixed with a special stereotaxic frame 7 which, in turn, is fixedly connected to the operating table 8. This stereotaxic frame 7 is also used as a localization aid during the development of a preoperative diagnostic record and therefore makes possible the correlation of this diagnostic data record with the observed field of view.

Figure 2:
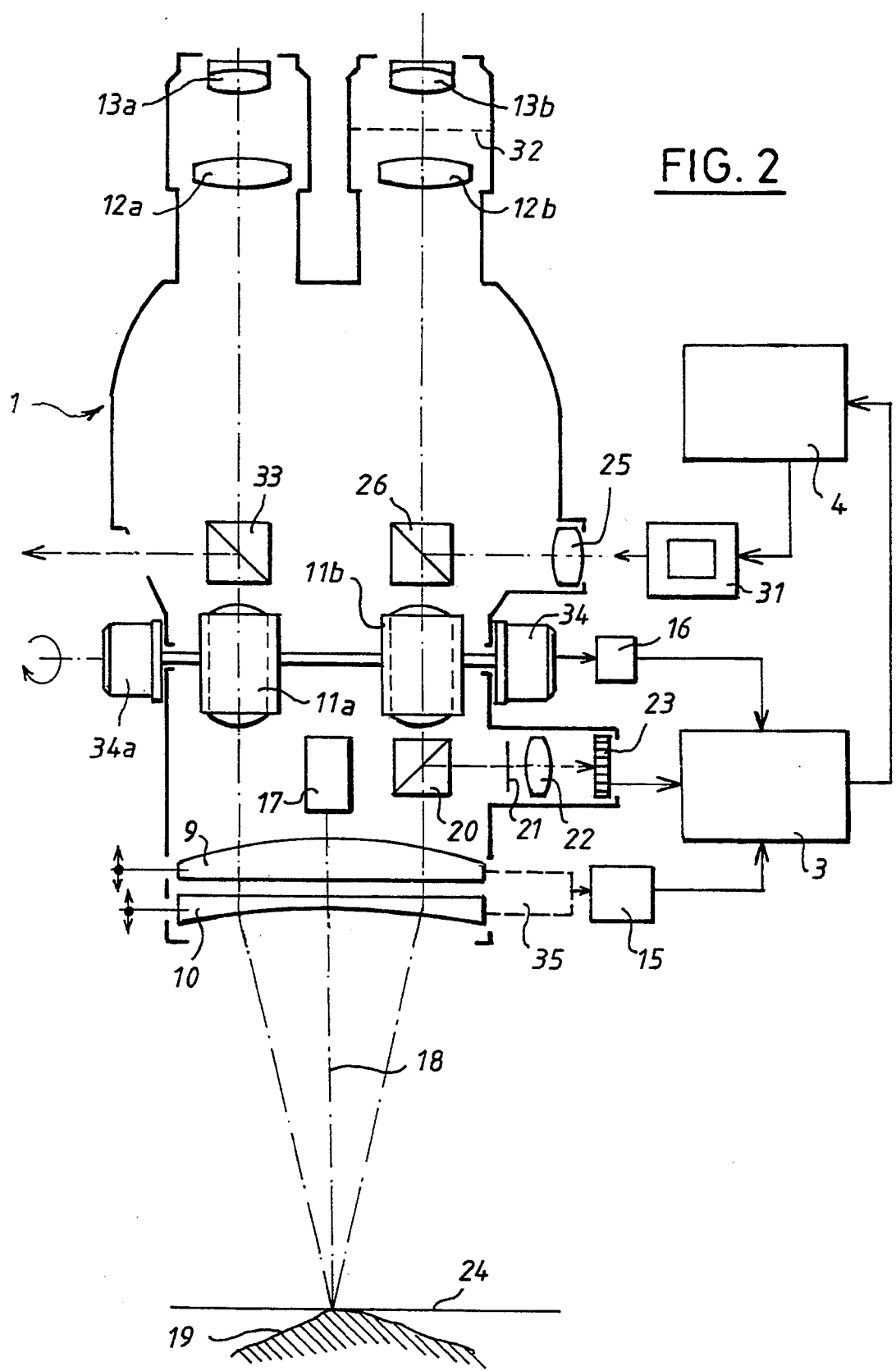
FIG. 2 is a front elevation schematic representation of the surgical microscope of FIG. 1.

FIG. 2 shows a front elevation view of an embodiment of the surgical microscope according to the invention. In addition, the necessary evaluation units for the operation of such a surgical microscope 1 for stereotactic computer-supported microsurgery are also shown. The surgical microscope 1 of the invention includes a two-part primary objective comprising a converging lens 9 and a diverging lens 10 for the two stereoscopically separated viewing beam paths. The two primary objective lenses (9, 10) can be displaced relative to each other along the optical axis 18 for focusing.

In addition, a zoom system (11a, 11b) for each of the two viewing beam paths is provided for changing the magnification setting. Parallel lenses (12a, 12b) and ocular lenses (13a, 13b) are mounted in each of the two viewing beam paths. Detectors (15, 16) are provided for determining the actual optical system data and detect the actual setting of the zoom system (11a, 11b) and the primary objective (9, 10) on the respective displacement elements (34, 34a) corresponding thereto and transmit this setting to the computer of the process-control unit 3.

A position-detecting system which operates pursuant to the laser triangulation principle is mounted between the primary objective (9, 10) and the zoom system (11a, 11b). The laser beam generated by a laser diode (not shown in FIG. 2) is projected onto the object surface 19 via a deflecting mirror 17 and through the primary objective (9, 10). The laser light scattered by the object surface 19 is coupled out of one of the viewing beam paths with the aid of out-coupling element 20. The out-coupled laser light is imaged on a suitable position-resolving detector 23 via a filter 21 and a projection lens 22. The position-resolving detector can be realized, for example, by a CCD-line array, a CCD-surface array or position-sensitive detectors (PSD). The position-detecting system shown here is built up on an optical basis and is not specific to the invention per se. Alternatives in the arrangement of the in-coupled and out-coupled beam paths are also possible or other known optical position-detecting systems are likewise possible which can be integrated into the optics of the surgical microscope.

The actual position of the reflected laser beam on the position detector 23 is graphically displayed on a TV-display 31 after the detector signals are evaluated in the computer of the process-control unit 3 and further processed in the image-processing unit 4. The desired position of the scattered laser beam on the position detector 23 is likewise displayed on the TV-display 31. The scattered laser beam assumes the desired position when the plane 24 of the field of view and the marked object detail 19 lie in one plane. In order to now ensure a defined measurement of an object detail, the two graphic markings of actual position and desired position of the scattered laser beam must be brought into overlapping alignment on the position detector 23 by focusing the surgical microscope 1. Here, it is not essential to the invention as to how focusing takes place, that is, in addition to the focusing of the objective of variable focal length, a displacement of the complete surgical microscope 1 along the optical axis 18 is also possible when an objective of fixed focal length is used.

In order to provide the surgeon with the assistance needed for focusing, the graphical display on the TV-display 31 is reflected into at least one of the two viewing beam paths via an in-reflecting device. This in-reflection or in-coupling of the desired and actual positions of the laser beam on the position detector 23 takes place via a projection lens 25, an in-coupling element 26 and a barrel lens 12b into the intermediate image plane 32 of the binocular tube. Here, the observed field of view provided by the microscope and the graphical display of the desired and actual positions of the scattered laser beam on the position detector 23 are superposed on each other for the viewer. The defined position determination of the marked object detail on the optical axis 18 takes place only after said field of view and said positions have been brought into alignment by corresponding through-focusing of the surgical microscope 1. For this purpose, the detectors (15, 16) on the optical zoom system (11a, 11b) and the primary objective (9, 10) are read out and processed by the process-control unit 3. Together with the simultaneously obtained spatial and orientation coordinates of the surgical microscope 1 from the displacement and angle detectors (block 42) of the multi-link supporting stand, the defined position determination of the marked object detail or of the observed field of view is possible.

An increase in the precision of evaluation is obtained in that, during assembly of a surgical microscope of this kind in a reference measurement, the optical and mechanical deviations of the system are detected during through-focusing and are stored in order to be applied during the actual measurement for evaluation.

It is in addition possible to detect the observed field of view with a suitable camera and display the same on a diagnostic monitor via a second out-coupling element 33 in the second viewing beam path. After determining the coordinates of the observed field of view, a corresponding previously developed diagnostic image can be superposed on the diagnostic monitor. It is likewise possible, with the aid of image-processing unit 4 and TV-display 31, to superpose in the viewing beam path such a diagnostic image on the field of view determined with respect to coordinates.

Figure 3:
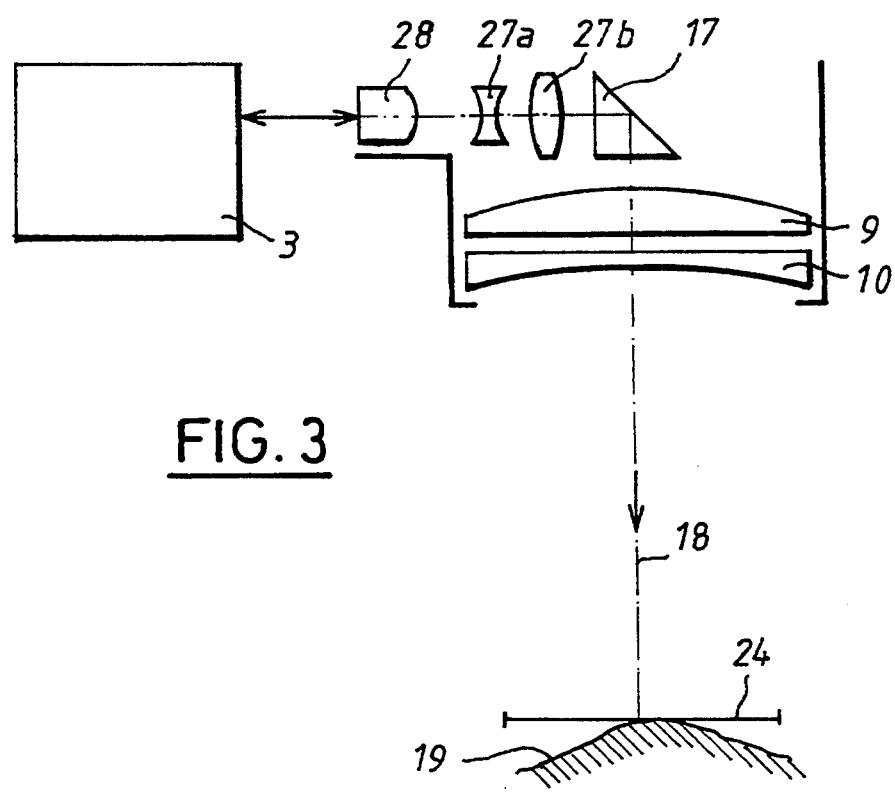
FIG. 3 is a side elevation view of the position-detecting system operating according to the laser-triangulation principle and disposed in the lower portion of the surgical microscope shown in FIGS. 1 and 2.

A side elevation view of the lower portion of the surgical microscope of FIG. 2 is shown in FIG. 3. A laser diode 28, which is controlled via the computer of the process-control unit 3, projects a laser beam onto a deflecting mirror 17 via two lenses (27a, 27b) which operate to expand and form the beam. The laser beam is then guided by the deflecting mirror 17 via the primary objective (9, 10) onto the surface 19 of the object. The arrangement of the position-detecting system in accordance with the laser triangulation principle is not essential to the invention in this embodiment.

In the embodiment shown in FIGS. 2 and 3, a laser diode 28 is used which emits in the infrared spectral range. This brings advantages for the detection of scattered laser rays since, with the aid of a wavelength-selective out-coupling element 20, the scattered laser beam can be separated from the viewing beam path in a defined manner. A filter 21 is provided forward of the position detector 23 and transmits only for the laser wavelength used. By means of this filter 21, it is in addition ensured that no scattered light from the ambient reaches the position detector 23 which could produce incorrect information.

Figure 4A:
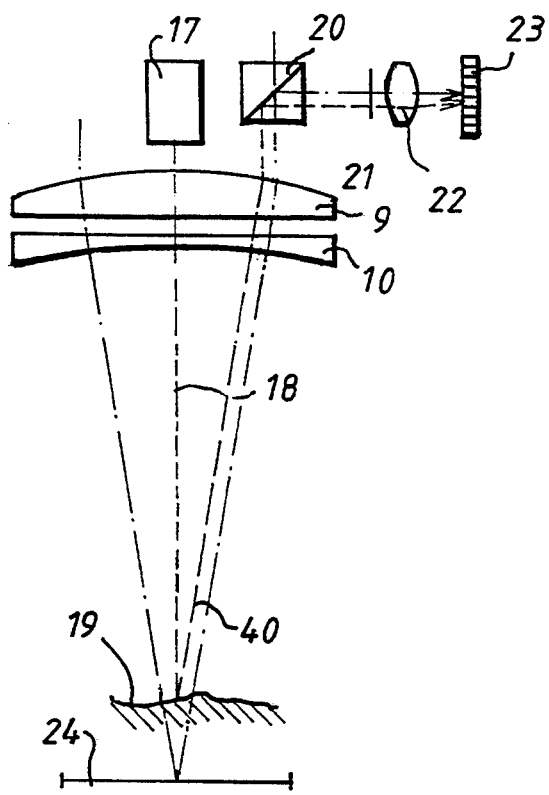
FIGS. 4a and 4b show various focusing positions.
Figure 4B:
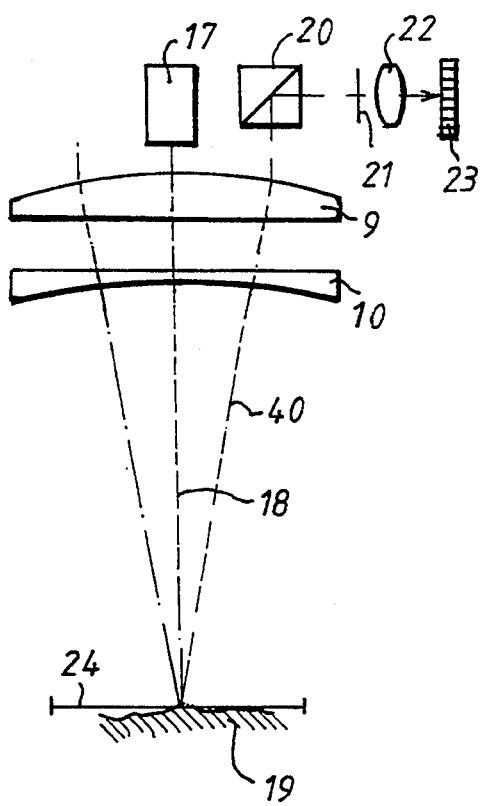
Figure 5A:
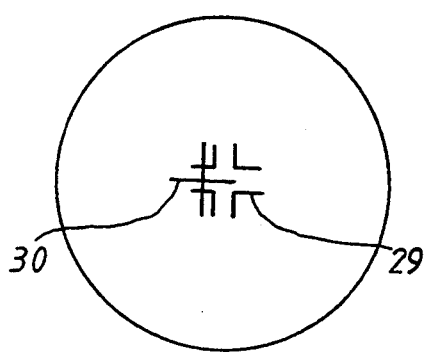
FIGS. 5a and 5b show the corresponding graphic displays on a TV-display or in a viewing beam path.
Figure 5B:
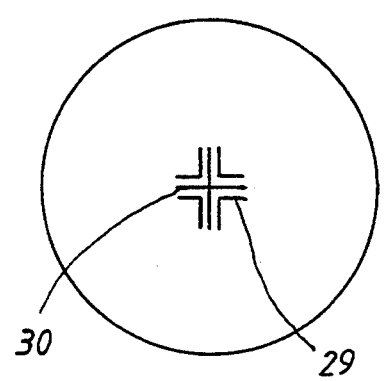

Various focusing states of such a system as well as the corresponding graphical displays on the TV-display or in the in-reflected intermediate image are shown in FIGS. 4a, 4b as well as in FIGS. 5a and 5b. In the case of FIG. 4a, marked object surface 19 and the plane 24 of the field of view of the surgical microscope are not in one plane. The laser beam is projected via the deflecting mirror 17 along the optical axis 18 onto the object surface 19. The scattered laser beam 40 is registered on the position detector 23 via primary objective (9, 10), out-coupling element 20, filter 21 and projection lens 22. The scattered laser beam 40 still does not show the position which is required for the precise measurement of the plane of the field of view.

One example of a graphical conversion of this state via the image-processing unit on a TV-display or the in-reflected intermediate image is shown in FIG. 5a. Open sighting cross lines 29 mark the desired state in the center of the field of view for the position of the scattered laser beam on the position detector 23 when the marked object surface 19 and the plane 24 of the field of view of the surgical microscope are coincident. The current actual position of the scattered laser beam on the position detector 23 is marked by the position of the cross 30 on the TV-display or in the in-reflected intermediate image. The surgeon now brings the two marks into alignment by through-focusing the optical system in order to obtain a defined position of the marked object detail on the optical axis 18. This state is shown in FIG. 4b as are the marks (29, 30) in FIG. 5b which were brought into alignment. As soon as coincidence is reached, the position of the plane 24 of the field of view relative to the surgical microscope 1 is determined with the aid of the optical system data read out of the corresponding detectors (15, 16).

Together with the determined spatial and orientation coordinates of the surgical microscope 1 and a previous calibration measurement, the defined determination of the viewed object detail in the patient coordinate system is then possible. During the previously carried out calibration measurement, the position of several known points in the patient coordinate system is determined with the aid of the surgical microscope 1 according to the invention. With these measured points, the position and orientation of the patient in space can be determined. Together with the field of view coordinates determined subsequently via the method pursuant to the invention, the correlation of the observed field of view with the corresponding diagnostic data is possible after an appropriate transformation of the coordinates is made.

As an alternative to the manual through-focusing of the surgical microscope, it is possible to carry out the described sighting method in the form of an automatic focusing with the process-control unit 3 taking over the through-focusing via a corresponding drive.

It is understood that the foregoing description is that of the preferred embodiments of the invention and that various changes and modifications may be made thereto without departing from the spirit and scope of the invention as defined in the appended claims.

What is claimed is:

1. A surgical microscope arrangement for computer-supported stereotactic microsurgery, the arrangement comprising:

a surgical stereomicroscope having an optical system defining two viewing beam paths for viewing an object defining an object plane;

detector means for monitoring said optical system to obtain a first signal indicative of the setting of said optical system;

an optical position detection system integrated into said optical system for detecting the position of said object plane and for supplying a second signal indicative of said position;

process control means for processing said first and second signals and supplying an output signal; and, an image-processing unit for converting the output signal of said process control means into display signals for providing a graphic display.

2. The surgical microscope arrangement of claim 1, said optical position detection system being configured to operate pursuant to the laser triangulation principle.

3. The surgical microscope arrangement of claim 1, said image-processing unit including a TV-display for providing a graphic display of said display signals.

4. The surgical microscope arrangement of claim 3, further comprising an in-reflecting device for coupling said graphic display into one of said viewing beam paths, said in-reflecting device including a projection optic for receiving and transmitting said graphic display from said TV-display; and, an in-coupling element mounted downstream of said projection optic and being disposed in said one beam path for coupling said graphic display into said one beam path.

5. The surgical microscope arrangement of claim 1, said optical system including magnification means mounted in said viewing beam paths and an objective arranged downstream of said magnification means; and, said optical position detection system being mounted between said magnification means and said objective.

6. The surgical microscope arrangement of claim 5, said optical position detection system comprising:

a laser light source for generating a laser light;

optical means for receiving said light and forming a laser light beam therefrom; and, a deflecting element mounted between said magnification means and said objective for directing said laser light beam through said objective to said object.

7. The surgical microscope arrangement of claim 5, said optical position detecting system comprising laser beam means for directing a laser light beam through said objective onto said object where the light of the laser light beam backscatters from said object and enters said viewing beam paths; out-coupling means arranged in one of said viewing beam paths for coupling the backscattered light out of said one viewing beam path; imaging optic means for receiving and transmitting the backscattered light; and, a position-resolving detector for receiving the light transmitted by said imaging optic means.

8. The surgical microscope arrangement of claim 1, further comprising: a multi-link stand and said stereomicroscope being mounted on said multi-link stand; and, sensor means for supplying signals indicative of the actual spatial coordinates and orientation of said surgical stereomicroscope.

9. A method of operating a surgical microscope arrangement for computer-supported stereotactic microsurgery, the arrangement including a surgical stereomicroscope having an optical system with two viewing beam paths for viewing a detail of an object defining an object detail plane passing through said object detail, and the method comprising the steps of:

continuously determining the spatial coordinates and the orientation of said surgical stereomicroscope and supplying a first signal indicative thereof to a process control unit having an output;

continuously detecting the current position of said object plane via an optical position detection system and supplying a second signal indicative thereof to said process control unit;

applying the output of said process control unit to an image-processing unit for converting the output into display signals graphically displaying said current position of said object detail plane on a TV-display as a first display;

graphically displaying the current position of the plane of the field of view observed through the surgical stereomicroscope on said TV-display as a second display via said process-control unit and said image-processing unit;

focusing or defocusing said optical system of said surgical stereomicroscope to bring said first and second displays into overlapping alignment with each other;

determining the optical system data of said optical system utilizing detectors monitoring said optical system and supplying a third signal indicative thereof to said process control unit;

determining the position of said object detail plane relative to said surgical stereomicroscope with the aid of said optical system data; and, determining the spatial coordinates of said object detail plane from the following: the coordinates of said object detail plane relative to said surgical stereomicroscope, said spatial coordinates of said surgical stereomicroscope and said orientation of said surgical stereomicroscope after a coordinate transformation.

10. The method of claim 9, said first and second graphic displays being reflected into at least one of said viewing beam paths.

11. The method of claim 9, further comprising the step of superposing an image from a preoperative diagnostic method on said field of view after determining the coordinates of the object detail in space and considering the magnification of said optical system; and, said image having coordinates corresponding to said coordinates of said object detail.

12. The method of claim 9, wherein the graphic display of the position of the image plane takes place in the center of the field of view of the image section being viewed.

13. The method of claim 9, further comprising the steps of: conducting a reference measurement to detect optical and mechanical deviations of the optical system while through focusing; storing said deviations and considering said deviations to correct the instantaneously detected measured values.

14. The method of claim 9, wherein said focusing or defocusing of said optical system takes place automatically via said process control unit.

* * * * *